(12) United States Patent
Ikeuchi et al.

(10) Patent No.: US 12,215,308 B2
(45) Date of Patent: Feb. 4, 2025

(54) CHARGED PARTICLE BEAM APPARATUS AND CELL EVALUATION METHOD

(71) Applicant: Hitachi High-Technologies Corporation, Tokyo (JP)

(72) Inventors: Akira Ikeuchi, Tokyo (JP); Shigeru Kawamata, Tokyo (JP); Hiromi Mise, Tokyo (JP); Akira Sawaguchi, Miyazaki (JP)

(73) Assignee: Hitachi High-Tech Corporation, Tokyo (JP)

( * ) Notice: Subject to any disclaimer, the term of this patent is extended or adjusted under 35 U.S.C. 154(b) by 1289 days.

(21) Appl. No.: 16/604,908

(22) PCT Filed: Apr. 14, 2017

(86) PCT No.: PCT/JP2017/015230
§ 371 (c)(1),
(2) Date: Oct. 11, 2019

(87) PCT Pub. No.: WO2018/189877
PCT Pub. Date: Oct. 18, 2018

(65) Prior Publication Data
US 2020/0056141 A1    Feb. 20, 2020

(51) Int. Cl.
*C12M 1/34* (2006.01)
*G01N 33/483* (2006.01)
(Continued)

(52) U.S. Cl.
CPC ......... *C12M 41/46* (2013.01); *G01N 33/4833* (2013.01); *G06T 7/62* (2017.01);
(Continued)

(58) Field of Classification Search
CPC ..... C12M 41/46; C12Q 1/04; G01N 33/4833; H01J 37/222; H01J 37/26; H01J 2237/221; G06T 7/62; G06T 7/64
See application file for complete search history.

(56) References Cited

U.S. PATENT DOCUMENTS

2002/0024022 A1* 2/2002 Kageyama .......... H01J 37/3045
250/492.22
2008/0279441 A1 11/2008 Matsuo et al.
(Continued)

FOREIGN PATENT DOCUMENTS

JP      2007-020449 A    2/2007
JP      5333635 B1      11/2013
(Continued)

OTHER PUBLICATIONS

Japanese-language Office Action issued in Japanese Application No. 2019-512140 dated Nov. 4, 2020 with English translation (10 pages).
(Continued)

*Primary Examiner* — Lydia Edwards
(74) *Attorney, Agent, or Firm* — Crowell & Moring LLP (57) ABSTRACT

Provided is a charged particle beam apparatus capable of more objectively and highly accurately calculating a feature of a cell from an observation image of a cell and evaluating a cell. The charged particle beam apparatus includes an image acquisition unit 18 that acquires an image of a cell, a contour extraction unit 19 that extracts a contour of the image, a feature calculation unit 20 that calculates a morphological feature of the contour based on the contour and calculates the feature of an internal structure such as a cytoplasm contained in an internal area of the contour, and a determination unit 21 that determines quality and/or functionality of the cell based on the feature, and can objectively
(Continued)

and highly accurately evaluate the quality and/or the functionality of the cell included in the captured image.

5 Claims, 7 Drawing Sheets (51) Int. Cl.
| | |
|---|---|
| G06T 7/60 | (2017.01) |
| G06T 7/62 | (2017.01) |
| G06T 7/64 | (2017.01) |
| H01J 37/22 | (2006.01) |
| H01J 37/26 | (2006.01) |
| H01J 99/00 | (2006.01) |

(52) U.S. Cl.
CPC .............. *G06T 7/64* (2017.01); *H01J 37/222* (2013.01); *H01J 37/26* (2013.01); *H01J 2237/221* (2013.01)

(56) References Cited

U.S. PATENT DOCUMENTS

| | | |
|---|---|---|
| 2012/0114219 A1 | 5/2012 | Nakagawa et al. |
| 2013/0002847 A1* | 1/2013 | Zahniser ............ G01N 15/1475 345/682 |
| 2015/0187077 A1 | 7/2015 | Ozaki et al. |
| 2015/0219543 A1* | 8/2015 | Yamauchi .............. G06V 20/69 356/335 |
| 2015/0275176 A1 | 10/2015 | Kobayashi et al. |

FOREIGN PATENT DOCUMENTS

| | | |
|---|---|---|
| JP | 2014-161254 A | 9/2014 |
| JP | 2015-198644 A | 11/2015 |
| JP | 2016-504339 A | 2/2016 |
| WO | WO 2011/010449 A1 | 1/2011 |
| WO | WO 2014/100779 A1 | 6/2014 |

OTHER PUBLICATIONS

International Search Report (PCT/ISA/210) issued in PCT Application No. PCT/JP2017/015230 dated Jul. 18, 2017 with English translation (four (4) pages).

Japanese-language Written Opinion (PCT/ISA/237) issued in PCT Application No. PCT/JP2017/015230 dated Jul. 18, 2017 (five (5) pages).

Manabe et al., "Automated Computation of Parameters for Level Set Method Intended for Image Captured by Electron Microscope", The 73rd National Convention of Information Processing Society of Japan, 2011, vol. 6T-7, pp. 2-519 to 2-520 with English translation (12 pages).

* cited by examiner

| FEATURE DATA | REFERENCE VALUE |
|---|---|
| MORPHOLOGICAL COMPLEXITY | < 49 |
| OCS AREA RATIO | 0.05 ~ 0.20 |
| OCS EXPANSION DEGREE | < 0.35 |
| DEEP DYEING REGION AREA RATIO | 0.05 < |

71

| PLATELET ID | EVALUATION RESULT | FEATURE DATA | | | |
|---|---|---|---|---|---|
| | | MORPHOLOGICAL COMPLEXITY | OCS AREA RATIO | OCS EXPANSION DEGREE | DEEP DYEING REGION AREA RATIO |
| P1R1 | GOOD | 13.2 (○) | 0.15 (○) | 0.05 (○) | 0.16 (○) |
| P1R2 | BAD | 25.4 (○) | 0.22 (×) | 0.15 (○) | 0.31 (○) |
| P1R3 | BAD | 59.0 (×) | 0.70 (×) | 0.88 (×) | 0.02 (×) |
| ... | ... | ... | ... | ... | ... |

72

CHARGED PARTICLE BEAM APPARATUS AND CELL EVALUATION METHOD

TECHNICAL FIELD

The present invention relates to a charged particle beam apparatus, a cell evaluation method using the same, and a program thereof.

BACKGROUND ART

In recent years, as a technique related to regenerative medicine, a method has been proposed for producing specific cells (differentiated cells) by culturing undifferentiated pluripotent stem cells represented by induced pluripotent stem (iPS) cells and embryonic stem (ES) cells and differentiating and inducing pluripotent stem cells. At this time, a charged particle beam apparatus represented by an optical microscope or a transmission electron microscope (TEM) is used to evaluate whether a desired cell is produced.

In particular, since a charged particle beam apparatus uses a charged particle beam such as an electron beam or an ion beam having a wavelength shorter than that of light, it is possible to observe an intracellular microstructure having a size on the order of several nanometers to several hundred nanometers, which cannot be observed by an optical microscope.

For example, PTL 1 discloses an example in which cells are evaluated by observing differentiated cells differentiated and induced from undifferentiated cells and products of the differentiated cells under a transmission electron microscope and confirming an internal structure specific to the desired differentiated cells. Further, PTL 2 discloses an image processing apparatus that extracts a plurality of cells each having a nucleus for a captured image obtained by capturing a sample containing a target cell with an optical microscope, calculates a feature related to a size of at least one of the cell and the nucleus from the image, and determines whether the cell extracted using a threshold value is a desired cell.

PRIOR ART LITERATURE

Patent Literature

PTL 1: JP-A-2015-198644
PTL 2: Japanese Patent No. 5333635

SUMMARY OF INVENTION

Technical Problem

In PTL 1, an image of a differentiated cell is captured by a transmission electron microscope to determine that the differentiated and induced cell is a desired cell, and it is determined whether an internal structure specific to the desired cell is present inside the cell with appropriate distribution and proportion by an expert with knowledge of cell morphology. Visual inspection determined by the eyes of such a person has poor objectivity in terms of quality assurance, and an enormous inspection time is required when the number of tests increases.

In PTL 2, with regard to the problem of objectivity and inspection time in such visual inspection, a plurality of cells each having a nucleus are extracted from a captured image obtained by capturing a sample containing a target cell with an optical microscope, a feature related to a size of at least one of the cell and the nucleus from the image is calculated, and it is determined whether the cell extracted using a threshold value is the desired cell.

However, in the case of the captured image of the optical microscope, a target cell is determined by using a nucleus of several micrometers in size as a clue, and thus when the internal structure specific to the desired cell is a cytosolic microstructure such as microfilaments (about 6 nanometers), ribosomes (about 20 nanometers), and secretory granules (tens to hundreds of nanometers), resolution limit of the optical microscope could not image the microstructure, and the determination could not be carried out in some cases.

An object of the invention is to solve the above problems and to provide a charged particle beam apparatus, a cell evaluation method using the same, and a program thereof, which can more objectively and highly accurately calculate the feature of a cell from an observation image of a cell, and evaluate cells.

Solution to Problem

According to an aspect of the invention, there is provided a charged particle beam apparatus including an acquisition unit that acquires an image of a cell, and a determination unit that determines the quality and/or functionality of the cell based on a feature in the acquired image.

In order to achieve the above object, the invention provides a cell evaluation method by an image processing apparatus. The image processing apparatus acquires a cross-sectional image of a cell based on a signal detected by a detector of a charged particle beam apparatus, and determines the quality and/or the functionality of the cells based on a feature in the acquired cross-sectional image.

Further, in order to achieve the above object, the invention provides a cell evaluation program executed by the image processing apparatus, in which a cross-sectional image of a cell is acquired by a signal detected by a detector of a charged particle beam apparatus, and causes the image processing apparatus to operate so as to determine the quality and/or functionality of the cell based on a feature in the acquired cross-sectional image.

Advantageous Effect

According to the invention, it is possible to objectively and highly accurately evaluate the quality and/or the functionality of the cell included in a captured image.

DESCRIPTION OF EMBODIMENTS

Hereinafter, embodiments of the charged particle beam apparatus of the invention will be sequentially described with reference to the drawings. In the description, a scanning electron microscope (SEM) will be described as an example of the charged particle beam apparatus, but the charged particle beam apparatus of the invention is not limited to the scanning electron microscope. The charged particle beam apparatus may set an observation range on a sample for acquiring an observation image by the charged particle beam apparatus on a captured image of the sample acquired by a capture apparatus as a visual field range, and, on the other hand, may irradiate the observation range on the sample corresponding to the visual field range with the charged particle beam and acquire the observation image of the sample. For example, the charged particle beam apparatus may include a scanning ion microscope, a scanning transmission electron microscope, a transmission electron microscope, a combined apparatus of the above apparatuses and a sample processing apparatus, or an analysis and inspection apparatus to which the above apparatuses are applied.

In addition, although platelets are described as examples of a target cell to be evaluated as differentiated cells differentiated and induced from pluripotent stem cells (undifferentiated cells) such as iPS cells and ES cells in the description, the cell to be evaluated of the invention is not limited to the platelets. The differentiated cells, which are cells to be evaluated according to the invention, can evaluate the quality and/or functionality of the cells based on the morphology of the cell and/or the feature of the internal structure, which may include, for example, neural stem cells, cardiomyocytes, insulin-producing cells, stem cells, hematopoietic stem cells, or cells of the cornea, retina, bone, cartilage, muscle, kidney, and the like.

Note that, the platelets are produced by mature megakaryocytes after hematopoietic stem cells differentiate into megakaryocytes. That is, white blood cells, red blood cells, and platelets are produced by differentiating the hematopoietic stem cells. That is, the pluripotent stem cells such as iPS cells and ES cells, which are undifferentiated cells, differentiate into various stem cells such as hematopoietic stem cells and neural stem cells which are undifferentiated cells, and then differentiate into various cells such as platelets, red blood cells, white blood cells, cardiomyocytes, insulin-producing cells, corneal cells, retinal cells, osteocytes, chondrocytes, muscle cells, kidney cells, which are differentiated cells.

First Embodiment

<System Configuration Example of Charged Particle Beam Apparatus and Cell Evaluation Flow>

Figure 1:
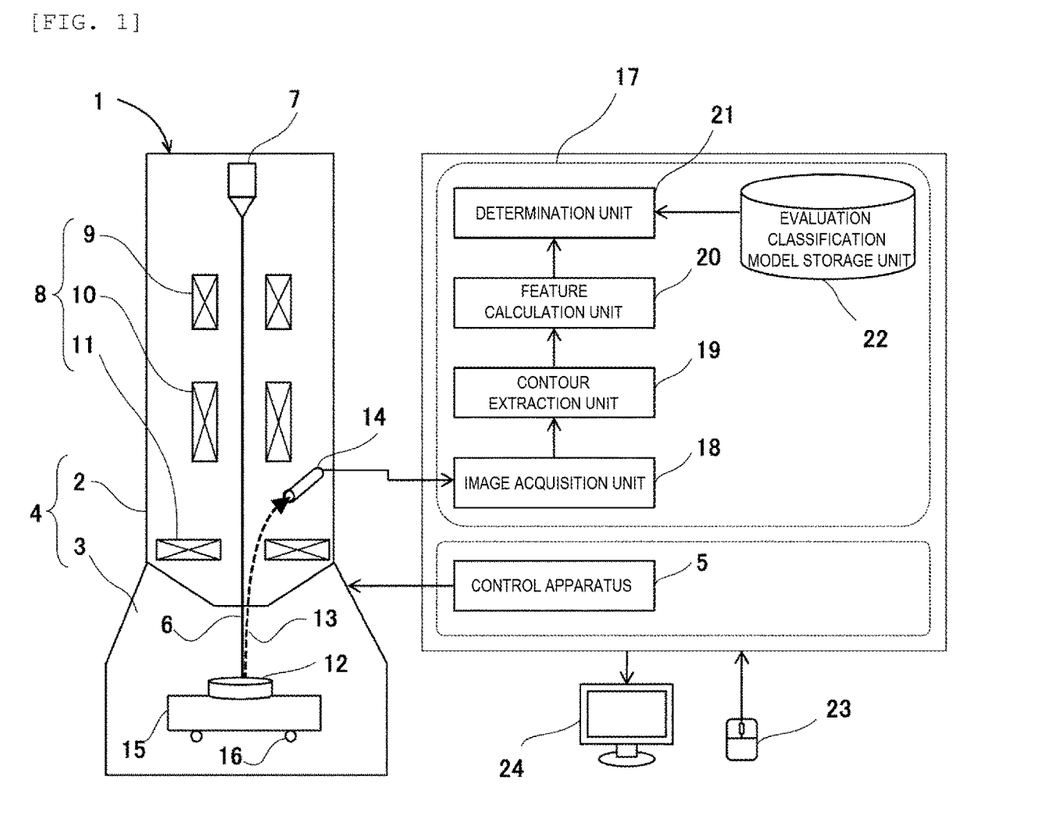
FIG. 1 is a diagram showing an example of a system configuration of a charged particle beam apparatus according to a first embodiment.

FIG. 1 is a schematic diagram of an example of a scanning electron microscope which is a charged particle beam apparatus according to a first embodiment.

A scanning electron microscope 1 includes a microscope apparatus main body 4 in which a lens barrel 2 and a sample chamber 3 are integrated, and a control apparatus 5 that controls each unit in the scanning electron microscope apparatus main body. The lens barrel 2 is provided with an electron gun 7 that emits an electron beam 6, and an electron optical system 8 that controls irradiation of the electron beam 6.

The electron optical system 8 includes a condenser lens 9 that focuses the electron beam 6 emitted from the electron gun 7, a deflector 10 that scans the electron beam 6, and an objective lens 11 that focuses the electron beam 6 such that the electron beam 6 is focused on a surface of a sample 12. In the illustrated example, a detector 14 that detects a signal 13 such as a reflected electron or a secondary electron generated by irradiating the sample 12 with the electron beam 6 is also provided.

The sample chamber 3 has a configuration in which the sample 12 is accommodated by loosening an inlet/outlet port (not shown) that can be opened and closed, and the sample 12 is provided with a sample stage 15. The sample stage 15 includes a sample moving mechanism 16 which moves the sample 12 in the sample chamber 3, for example, in a horizontal plane and a plane linear direction, or rotates or tilts the sample 12 to displace the position and the direction of the sample 12 in the sample chamber 3. The sample moving mechanism 16 and the electron optical system 8 are controlled by the control apparatus 5, the electron beam 6 is irradiated to an arbitrary position of the sample 12, and the generated signal 13 is detected by the detector 14, thereby performing electron microscopy observation at any position and magnification of the sample. Here, the magnification may be a width of a Field of View (FOV) or a length (pixel size) indicated by one pixel in the case of a digital image.

A image processing apparatus 17 includes an image acquisition unit 18 that converts a signal such as reflected electrons obtained by the detector 14 into observation image data (hereinafter, referred to as electron microscopy image data), a contour extraction unit 19, a feature calculation unit 20, a determination unit 21, and an evaluation classification model storage unit 22. The evaluation classification model storage unit 22 can be constituted by a storage unit capable of storing not only an evaluation classification model, but also the electron microscopy image data acquired by the image acquisition unit 18, the contour data extracted by the contour extraction unit 19, the feature data calculated by the feature calculation unit 20, and the like.

The electron microscopy image data is read from the image acquisition unit 18 into the contour extraction unit 19 and is subjected to area division (segmentation) processing by image processing. The contour extraction is first performed on outlines of individual platelets included in the electron microscopy image data. Thus, the contour (polygon) data of the individual platelet outlines is calculated from the electron microscopy image data. Next, by performing contour extraction again in an internal area of the individual platelets, contour data of internal structures such as cell organelles, such as secretory granules and an Open Canalicular System (OCS), contained inside the platelets is calculated. Details of the contour extraction processing executed by the contour extraction unit 19 will be described later.

The feature calculation unit 20 assigns IDs to the individual platelets calculated by the contour extraction unit 19, and calculates feature data indicating a morphological feature such as an area, a diameter, and a circumference based on an outline associated with a specific platelet ID, and contour data of an internal structure of cell organelles contained in the platelets such as secretory granules and open canalicular system, and/or feature data such as distribution, an area ratio, and a degree of expansion of secretory granules and an open canalicular system by using an area ratio of the area of the platelet to the secretory granules and a ratio of the maximum diameter of the open canalicular system to the diameter of the platelet. Details of the feature calculation processing and each feature executed by the feature calculation unit 20 will be described later.

Here, a length of the largest line segment connecting two points on the outer periphery of the contour indicated by the contour data of platelets and passing through the center of gravity of the contour is defined as a diameter. Further, a length of the smallest line segment connecting the two points on the outer periphery of the contour indicated by the contour data and passing through the center of gravity of the contour may be defined as a minimum diameter, and a length of the line segment connecting the two points on the outer periphery of the contour indicated by the contour data and passing through the center of gravity of the contour may be measured within 360 degrees in any angle, and an average value may be defined as an average diameter.

Further, the maximum diameter calculates a minimum rectangle surrounding the entire contour indicated by the contour data, and defines a length of the long side of the rectangle as the maximum diameter. Although the value of the diameter is calculated by using the center of gravity of the contour, an effective measurement value may not be obtained when the center of gravity is outside the contour. Therefore, when obtaining the size information of the open canalicular system, the degree of expansion of the open canalicular system can be more accurately quantified by using the maximum diameter using a circumscribed quadrangle (the smallest rectangle surrounding the entire contour).

The determination unit 21 determines the quality and/or functionality of the platelets by evaluating each feature data associated with the individual platelet IDs according to the evaluation classification model stored in the evaluation classification model storage unit 22. Further, information such as the evaluation classification model used in the determination unit 21, a determination value and a determination reference value used for evaluation can be edited by a user via an input unit 23, and information of a determination result and the evaluation classification model is displayed to the user via a display unit 24. The details of the evaluation classification model used in the determination unit 21 and a determination method will be described later. Further, the display unit 24 displays an evaluation result of each platelet evaluated by the determination unit 21 and/or statistical information of the determination result of all platelets.

The control apparatus 5, the image processing apparatus 17, the input unit 23, the display unit 24, and the like may be realized using a personal computer (PC). In this case, the control apparatus 5 and the image processing apparatus 17 can be realized by executing programs of a central processing unit (CPU) of the PC, and a storage unit of the PC can store these operation programs and various data including the above evaluation classification model.

The above is an overview of each component of the system configuration example using the scanning electron microscope according to the first embodiment shown in FIG. 1. According to the scanning electron microscope of the present embodiment, it is possible to objectively and highly accurately evaluate the quality and/or the functionality of platelets included in the captured image by the user capturing the platelets and selecting an evaluation classification model suitable for evaluation purposes, and it is possible to evaluate platelets regardless of whether the user has expert knowledge of the cell morphology.

<Contour Extraction Unit>

Figure 2:
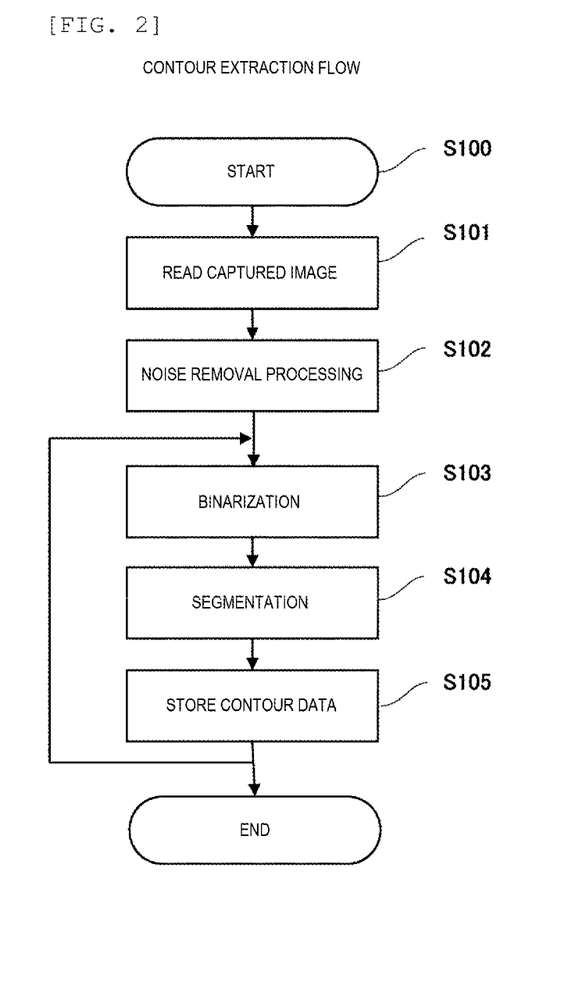
FIG. 2 is a flowchart of contour extraction processing of the configuration according to the first embodiment.

As an operation example of the contour extraction unit 19 in the configuration of the present embodiment, an operation example in a case where the electron microscopy image data is read will be described with reference to a flowchart in FIG. 2. Note that, the operation of the flowchart can be realized by execution of the programs, which are the image acquisition unit 18, the contour extraction unit 19, and the feature calculation unit 20 by the CPU described above.

First, the electron microscopy image data is read as a captured image (step S101). Next, noise removal processing of an image is performed for the purpose of enhancing the accuracy of the contour extraction (step S102). Specifically, filter processing for improving the accuracy of binarization processing and edge detection processing for the contour extraction, which will be described later, using well-known image processing techniques such as a median filter, a Gaussian filter, and a deconvolution filter, is performed. When a signal-to-noise ratio of the electron microscopy image data is sufficiently high for performing the contour extraction processing, the noise removal processing may be omitted.

Subsequently, by binarizing the electron microscopy image data after the noise removal processing, a contour extraction target and a background image are separated (step S103). Specifically, binarization is performed using a well-known image processing and image recognition technique such as Otsu binarization and a p-tile method.

Subsequently, segmentation (area division) of the binarized electron microscopy image data is performed, and the binarized area is divided into areas of individual platelets (step S104). When a platelet sample is captured, the platelets may be captured in an adjacent or contact state, and only the above binarization processing may erroneously recognize an aggregate of a large number of platelets as one platelet. Therefore, it is necessary to separate individual platelets from the platelet aggregates by the segmentation processing. Specifically, segmentation processing is performed using, for example, a method such as Watershed method, pattern matching, and a well-known image processing and image recognition technique using machine learning such as Deep Learning, and divided into contour data of an individual platelet.

Since the contour data of the individual platelet is calculated by the processing so far, the contour data corresponding to each platelet is stored in step S105. As a result, the contour data, which is shape data of the platelet outline, is associated with the individual platelet included in the electron microscopy image data.

The above is an example of processing when the outline of the individual platelet is extracted by the contour extraction unit. In the present embodiment, in order to improve the evaluation accuracy of the platelets, calculation and storage of contour data of not only the outline of the platelets but also cell organelles contained inside the platelets such as secretory granules and the open canalicular system is performed.

The calculation of the contour data of the internal structure such as the cell organelles is performed by repeatedly applying step S103 to step S105 described above, which is the contour extraction processing again for the internal area of the contour data of the already calculated platelet outline. For example, when calculating the contour data of the open canalicular system, a threshold value is set such that only the open canalicular system can be separated in the binarization condition, thereby collecting all the contour data of the open canalicular system included in the platelets. Similarly, by setting a threshold value such that only a deep dyeing region can be separated, the contour data of the deep dyeing region can be collected.

Figure 3:
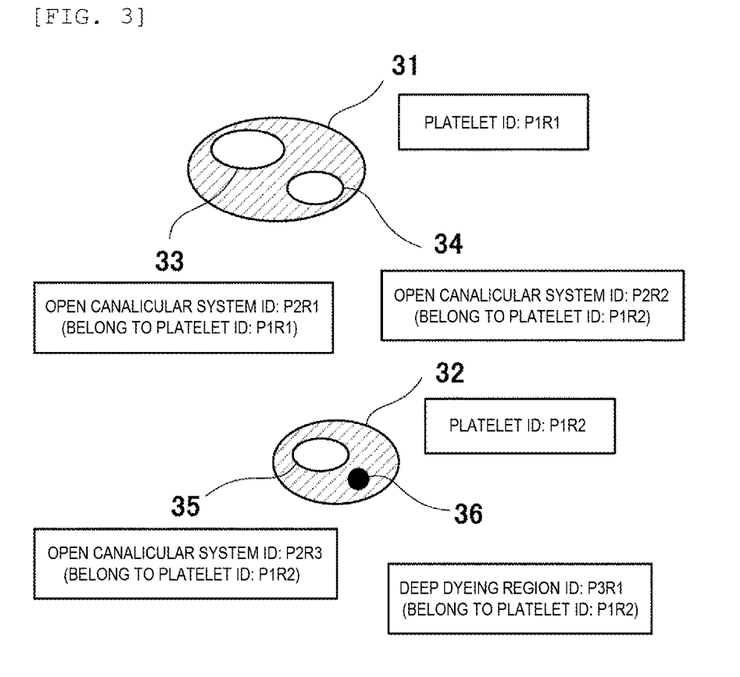
FIG. 3 is a diagram showing a correspondence relationship between contour data associated with a platelet ID according to the first embodiment.

Detected platelets 31, 32, open canalicular systems 33, 34, 35 inside the respective platelets, a deep dyeing region 36, and corresponding identifiers (ID) are schematically shown in FIG. 3. Then, as shown in FIG. 3, the collected contour data of the open canalicular system is stored in association with the platelet ID to which the open canalicular system belongs, and an ID is also assigned to each open canalicular system and stored. By performing the similar processing on all the platelets extracted from the electron microscopy image data, the contour data of the outline of individual platelets and the internal structure such as cell organelles (secretory granules, open canalicular system) contained in the platelets can be calculated and stored.

In the configuration and operation of the present embodiment, a granules, deep dyeing granules, secretory granules such as glycogen granules contained inside the platelets, and mitochondria, which are cell organelles specific to the platelets, are collectively defined as a deep dyeing region, and the contour data is calculated and stored. In addition, the contour data of the open canalicular system which is also a cell organelle specific to platelets is also calculated and stored. As a result, three contour data including the platelet outline, the deep dyeing region inside the platelets, and the open canalicular system are calculated and stored, and the feature calculation unit 20 calculates respective features.

Note that, it is not necessary to limit the contour extraction target to the platelet outline, the deep dyeing region, and the open canalicular system in order to evaluate the platelets, and the a granules, the deep dyeing granules, the glycogen granules, and the mitochondria may be individually set as the contour extraction target, or the cell organelles such as a dense tubular system or a micro tubule included in the platelets may be set as the contour extraction target. In addition, cytoplasm, inclusion body or paraplasm correlated to the quality and/or functionality of the platelets and quality may be set as a contour extraction target.

<Feature Calculation Unit>

When acquiring electron microscopy image data according to the configuration of FIG. 1, magnification data including the width of a Field Of View (FOV) or the length (pixel size) indicated by one pixel when converted to a digital image is acquired. Therefore, it is possible to digitize the morphological feature of the contour extraction target using the contour data calculated and stored by the contour extraction unit 19. For example, when the contour extraction target is a platelet outline, information related to the size of the area, diameter, maximum diameter, minimum diameter, circumference, and the like of the platelet outline can be calculated as the features.

In the present embodiment, an example in which a platelet sample is observed using the scanning electron microscope 1 is shown. In the observation including the internal structure of a cell using an electron microscope, a method of embedding a cell sample in a resin, preparing a slice sample by slicing the resin into slices of several micrometers in thickness, and observing a cross section of the slice sample is common. Therefore, for example, since it is expected that a diameter of the cross-sectional image of platelets found in the cross section of the slice sample and a true diameter of the platelets are different from each other, it is not possible to improve the accuracy of the cell evaluation only by the feature related to the size such as the diameter.

To solve the above problem, in the configuration of the present embodiment, in addition to the feature related to the size, as a feature capable of evaluating the quality and/or functionality of the platelets even from the cross-sectional image of the slice sample of the platelets, morphological complexity, an area ratio of open canalicular system, an expansion degree, and an area ratio of the deep dyeing region are calculated and stored as feature data. All feature data are stored in association with the individual platelet IDs as described above. Details of each feature will be described below.

Morphological Complexity

"Morphological complexity" is a feature showing roundness of the platelet outline. It is known that the platelets take a disc shape, like a foundation, in blood. As described above, in order to prepare a platelet sample by slicing a resin in which the platelets are embedded, it is expected that the cross section of the platelets to be observed is circular or elliptical. It is also known that the platelets have long protrusions when activated by external stimuli, which are entangled with each other to form aggregates (thrombi). Therefore, it can be determined that the platelets that lose roundness and become complicated in morphology are in an activated state. As a medical platelet product, a state in which the platelets are not activated is desirable.

The feature calculation unit 20 calculates "morphological complexity" by the following Formula (1).

$$(\text{Morphological complexity}) = (\text{circumference})^2 / (\text{area}) \quad (1)$$

Although the morphological complexity is calculated by Formula (1) in the present embodiment, the morphological complexity can be calculated as long as the morphological complexity can quantitatively express the roundness and complexity of platelets, for example, circularity or roundness may be used, and the morphological complexity may be calculated by combining the circumference, the area, the diameter, or the position of the center of gravity of the platelets.

Area Ratio of Open Canalicular System (OCS Area Ratio)

"OCS area ratio" is a feature showing a proportion of the open canalicular system inside the platelets. It is known that the life of platelets collected from human blood is about 4 days, and the area of the open canalicular system tends to increase for platelets near the end of life. Therefore, by calculating the OCS area ratio, it is possible to calculate the degree of increase of the open canalicular system, and it is possible to estimate whether the platelets are near the end of life.

The feature calculation unit 20 calculates the "OCS area ratio" by the following Formula (2).

$$(\text{OCS area ratio}) = (\text{total area of open canalicular system}) / (\text{area of platelets}) \quad (2)$$

Expansion Degree of Open Canalicular System (OCS Expansion Degree)

Figure 4:
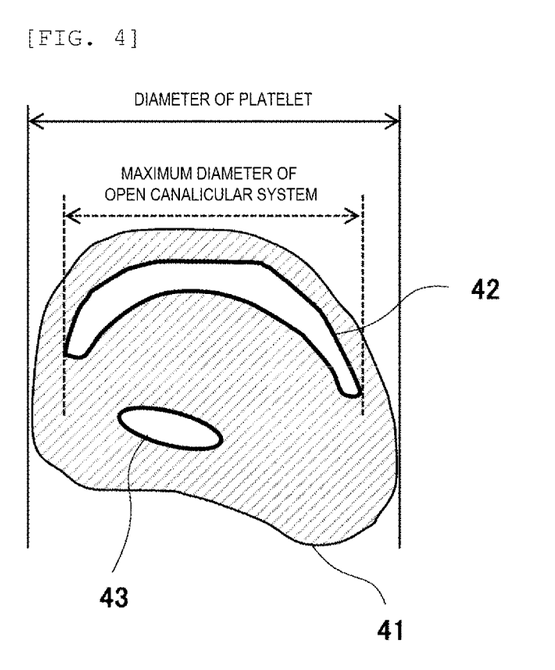
FIG. 4 is a diagram illustrating a definition of an expansion degree of an Open Canalicular System (OCS) according to the first embodiment.

"OCS Expansion Degree" is a feature showing the degree of expansion of the open canalicular system which is elongated and expanded in the open canalicular system inside the platelets, as shown in FIG. 4. Even when the area ratio of the above-described open canalicular system is low, an elongated open canalicular system 42 and another open canalicular system 43 are present inside a platelet 41, and when the maximum diameter of the elongated and expanded open canalicular system 42 exceeds 50% of the maximum diameter of the platelet outline, biochemical examination results of the present inventors show that it is highly likely that the hemostatic ability of the platelets is significantly reduced. Therefore, by calculating the OCS expansion degree, the platelets having low hemostatic ability can be selected. Note that, the hemostatic ability shows the size of the functionality of the platelets for hardening blood.

The feature calculation unit 20 calculates the "OCS expansion degree" by the following Formula (3).

(OCS expansion degree)=(maximum diameter of open canalicular system)/(diameter of platelets) (3)

At this time, the "maximum diameter of the open canalicular system" uses the value of the largest one of the maximum diameters of all open canalicular systems in the platelet.

In the present embodiment, although the OCS expansion degree is calculated by Formula (3), the OCS expansion degree can be calculated as long as it can quantitatively express the degree of expansion of the open canalicular system inside the platelets. For example, "the diameter of platelet" may be changed to "maximum diameter of platelet", and "maximum diameter of open canalicular system" may be changed to "largest diameter of open canalicular system". The definitional formula is not limited to Formula (3) as long as it shows the degree of expansion of the open canalicular system with respect to the platelet outline.

Area Ratio of Deep Dyeing Region (Deep Dyeing Region Area Ratio)

"Deep dyeing region area ratio" is a feature showing a proportion of the deep dyeing region inside the platelets. As described above, the deep dyeing region contains chemicals (secretions) closely related to the hemostatic mechanism of platelets, such as a granules and deep dyeing granules. Therefore, if a low value of the deep dyeing region area ratio is shown, such as 0%, 1%, 2%, 3%, 4%, 5%, the platelets can be estimated to have a low hemostatic ability.

The feature calculation unit 20 calculates the "deep dyeing region area ratio" by the following Formula (4).

(Deep dyeing region area ratio)=(total area of deep dyeing region)/(area of platelets) (4)

The components of the deep dyeing region defined for performing the evaluation of platelets need not be limited to a granules, deep dyeing granules, glycogen granules, mitochondria, and may include at least one or more cell organelles including secretions associated with the hemostatic mechanism. In addition, cytoplasm, inclusion body or paraplasm correlated to the quality and/or functionality of the platelets and quality may be defined instead of the deep dyeing region, and the area ratio may be calculated.

<Determination Unit>

As an operation example of the determination unit 21 in the present embodiment, an operation example when evaluating the quality and/or functionality of the platelets using the evaluation classification model stored in the evaluation classification model storage unit 22 based on the feature data will be described with reference to FIG. 5.

Figure 5:
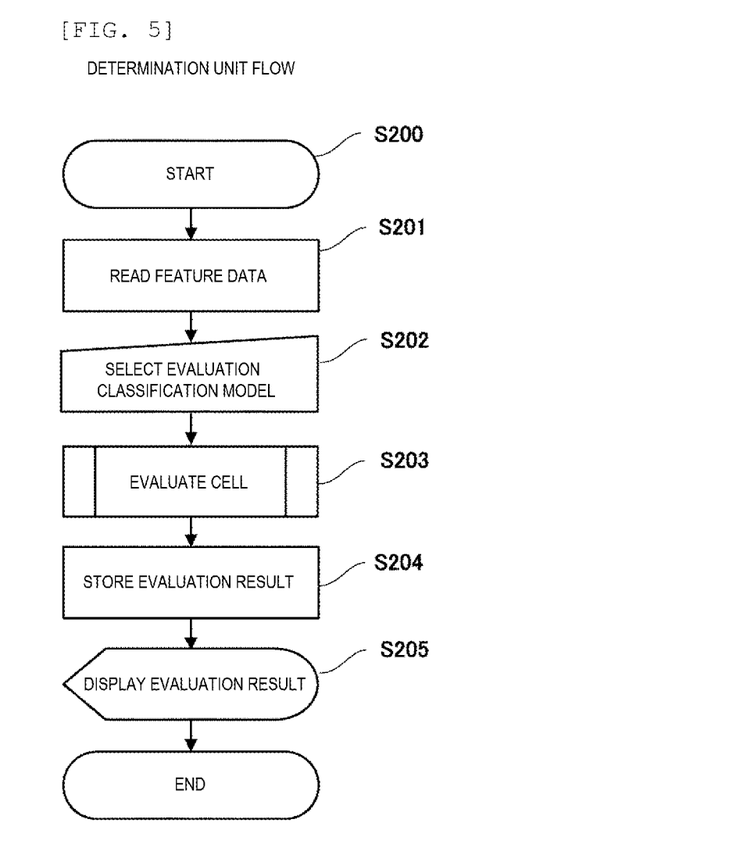
FIG. 5 is a flowchart showing determination processing of the configuration according to the first embodiment.
Figure 6:
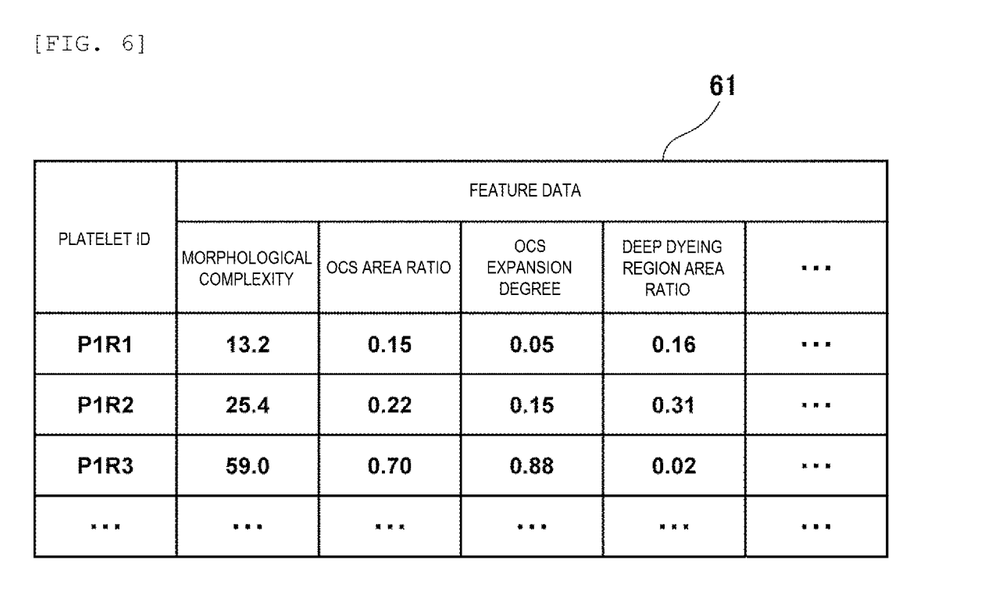
FIG. 6 is a diagram showing an example of a table in which feature data is stored in association with the platelet ID according to the first embodiment.

FIG. 5 is a flowchart showing the operation of the determination unit 21 in the configuration of the present embodiment. The operation can also be realized by program execution. First, the calculated and stored feature data is read (step S201). As shown in a feature data table 61 of FIG. 6, the feature data is a set of feature data associated with the platelet ID. Note that, as shown in FIG. 6, the storage format of the feature data only needs to store the feature data in a form associated with an individual platelet ID, and does not particularly specify the format or an item of the feature data included. Items of the feature data include at least one or more information such as the above-described morphological complexity, OCS area ratio, OCS expansion degree, deep dyeing region area ratio, feature related to size such as the area and the circumference, feature calculated by the feature calculation unit 20 and/or the average value, the total value, the maximum value, the minimum value, the statistic value of the feature.

Next, an arbitrary evaluation classification model is selected by the user via the input unit 23, and the evaluation classification model selected from the evaluation classification model storage unit 22 is read into the determination unit 21 (step S202). The evaluation classification model refers to a model that classifies the presence or absence of quality and/or functionality of the platelets based on the feature data calculated by the feature calculation unit 20. A reference value and a classification condition for each feature are recorded in the evaluation classification model storage unit 22, and evaluation of each platelet is performed according to the classification condition of the evaluation classification model (step S203).

An evaluation result of the platelets is stored in a form associated with each platelet ID (step S204), and the evaluation result is displayed to the user via the display unit 24 (step S205). Accordingly, the user can confirm the evaluation result of the platelets using an arbitrary evaluation classification model, and it is possible to objectively evaluate the quality and/or the functionality of the platelets based on morphological feature of the platelets, regardless of whether the user has expert knowledge of cell morphology.

Figure 7:
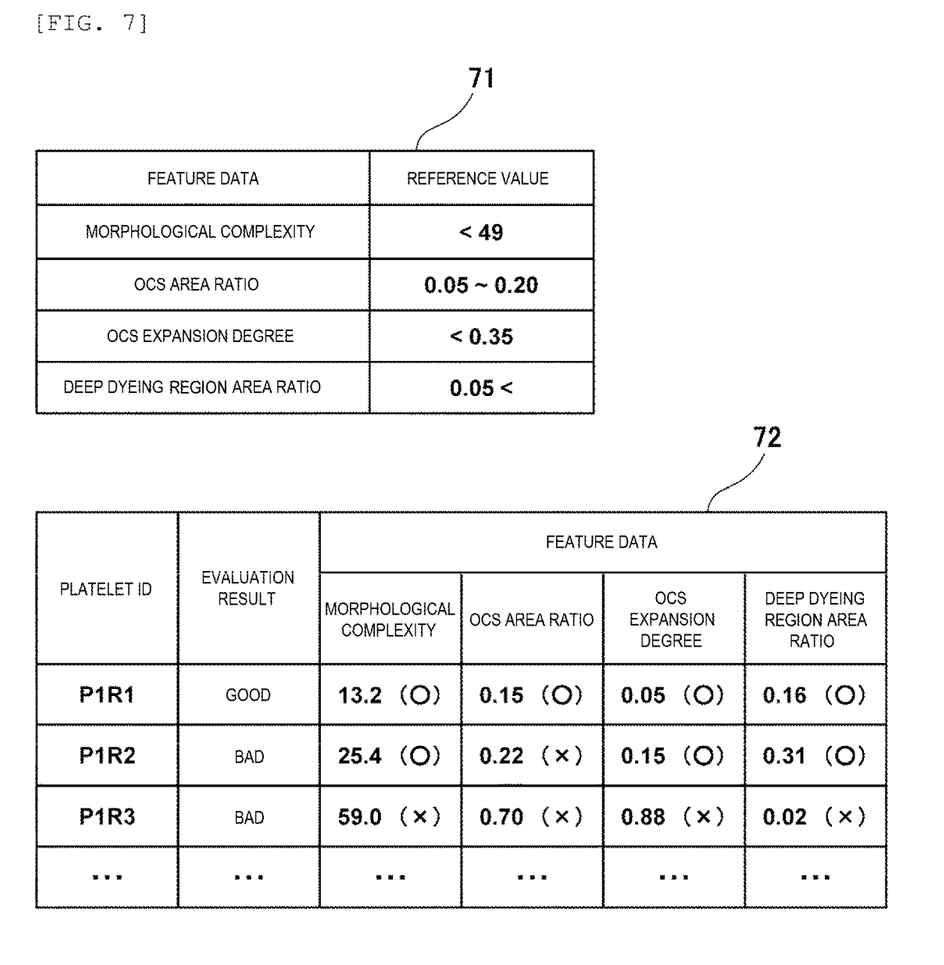
FIG. 7 is a diagram showing an example of a table that stores a reference value and a table that stores a result of performing quality determination of the platelet based on the reference value and the feature according to the first embodiment.

With reference to FIG. 7, a reference value model is described as an example of the evaluation classification model. The reference value model is an evaluation classification model that sets a reference value for each feature data, sets the evaluation result of the platelets to "good" only when all the feature data satisfy the reference values, and sets the evaluation result of the platelets as "bad" even when there is only one feature data that does not satisfy the reference value. FIG. 7 shows, by way of example, a reference value table 71 in which a reference value of a reference value model is stored, and a platelet information table 72 in which feature data associated with the platelet ID of each platelet and the evaluation result of the platelets are stored.

Results of performing the evaluation classification of the platelets based on the information of the reference value table by the determination unit 21 are stored in the platelet information table 72. In the example shown in FIG. 7, the feature used for the evaluation classification has four items of morphological complexity, OCS area ratio, OCS expansion degree, and deep dyeing region area ratio, and only the platelet ID "P1R1" satisfying the reference values for all the features is evaluated as "good". The information of the platelet information table 72 is displayed to the user via the display unit 24. At this time, a display item in the information display unit 24 of the platelet information table 72 only needs to include at least one or more of the platelet ID or the feature data in addition to the evaluation result, and the format thereof is not particularly limited. Further, as shown in FIG. 7, whether the value of each feature satisfies the reference value may be displayed to the user for each value of the feature.

Since the information of the platelet information table 72 is displayed to the user via the display unit 24, the user can view the evaluation result of the platelets and the value of each feature by the selected classification evaluation model for each platelet. Accordingly, the user can view not only the evaluation result of the classification evaluation model but also the correspondence between the reference value of classification evaluation and the feature of each platelet via the display unit 24, and can exam the platelet evaluation result and the validity of the evaluation result.

Although the reference value model described above is used for the evaluation classification model in the present embodiment, the evaluation classification model used for the evaluation of the platelets is not particularly limited to the reference value model as long as it can evaluate and classify the quality and/or functionality of the platelets using the feature data, and a classification model using a decision tree, a classification model created using a well-known machine learning method, or a classification model created by learning using Deep Learning may be used.

According to the invention, a cell image captured by the charged particle beam apparatus is used, by calculating the feature of the structure present inside the cell such as the cytoplasm in addition to the morphological feature of the cell outline, it is possible to objectively and highly accurately evaluate the quality and/or the functionality of the cells included in the captured image, and it is possible to evaluate the cells regardless of whether the user has expert knowledge of the cell morphology.

The invention is not limited to the embodiments described above, and includes various modifications. For example, the embodiments described above are described in detail for better understanding of the invention, and are not necessarily limited to those having all the configurations described above. In addition, a part of the configuration of one embodiment can be replaced with the configuration of another embodiment, and the configuration of another embodiment can be added to the configuration of one embodiment. In addition, a part of the configuration of the embodiment may be added, deleted, or replaced with another configuration.

Furthermore, although an example of creating a program for realizing a part or all of the configurations, functions, and control apparatuses described above is described, it is needless to say that a part or all of them may be realized by hardware, for example, by designing an integrated circuit. In other words, all or part of the functions of the control apparatus, the image acquisition unit, and the like may be realized by an integrated circuit such as an Application Specific Integrated Circuit (ASIC) or a Field Programmable Gate Array (FPGA) instead of the program.

REFERENCE SIGN LIST 1 scanning electron microscope
2 mirror
3 sample chamber
4 microscope apparatus main body
5 control apparatus
6 electron beam
7 electron gun
8 electron optical system
9 condenser lens
10 deflector
11 objective lens
12 sample
13 signal
14 detector
15 sample stage
16 sample moving mechanism
17 image processing apparatus
18 image acquisition unit
19 contour extraction unit
20 feature calculation unit
21 determination unit
22 evaluation classification model storage unit
23 input unit
24 display unit
41 platelet
42 elongated expanded open canalicular system
43 open canalicular system
61 feature data table
71 reference value table
72 platelet information table

The invention claimed is:

1. A charged particle beam apparatus comprising:
a computer processor; and
a memory storing a program that when executed by the computer processor causes the computer processor to:
acquire a cross-sectional image of a cell based on a signal, including a reflected electron or a secondary electron, detected by a detector of the charged particle beam apparatus;
determine a quality and/or a functionality of the cell based on a feature in the acquired image;
extract a contour of the cell based on the acquired image; and
calculate, as the feature, a morphological feature of the contour based on the extracted contour and a feature of an internal structure included in an internal area of the contour;
wherein the cell is a differentiated cell generated from undifferentiated cells;
wherein the differentiated cell is a platelet, the quality of the platelet shows a presence or absence of hemostatic ability, and the functionality of the platelet shows a size of the hemostatic ability; and
wherein the morphological feature of the contour shows roundness of the platelet outline, and the feature of the internal structure includes an area ratio of an open canalicular system of the platelet, an expansion degree of the open canalicular system, and an area ratio of a deep dyeing region of the platelet; and
wherein the computer processor determines the quality of the platelet and/or the functionality of the platelet based on the morphological feature and the feature of the internal structure.

2. The charged particle beam apparatus according to claim 1, wherein
the computer processor calculates the morphological feature showing the roundness of the platelet outline from the area and the circumference of the platelet.

3. The charged particle beam apparatus according to claim 1, wherein
the computer processor calculates as the feature, the area ratio of the open canalicular system, which is a proportion of a total area of the open canalicular system to the area of the platelet.

4. The charged particle beam apparatus according to claim 1, wherein
the computer processor calculates as the feature, the expansion degree of the open canalicular system, which is the maximum diameter of the open canalicular system with respect to the diameter of the platelet.

5. The charged particle beam apparatus according to claim 1, wherein
the computer processor calculates as the feature, the deep dyeing region, which is an area showing secretory granules and mitochondria of the platelets.

* * * * *